United States Patent [19]
Rogozinski

[11] Patent Number: 4,865,604
[45] Date of Patent: Sep. 12, 1989

[54] PROSTHETIC BONE JOINT

[76] Inventor: Chaim Rogozinski, 4453 Forest Dr. South, Jacksonville, Fla. 32216

[21] Appl. No.: 240,372

[22] Filed: Aug. 29, 1988

Related U.S. Application Data

[63] Continuation of Ser. No. 42,511, Apr. 27, 1987, abandoned, which is a continuation of Ser. No. 831,583, Feb. 21, 1986, abandoned.

[51] Int. Cl.$^4$ ............................ A61F 2/30; A61F 5/04
[52] U.S. Cl. .................................. 623/18; 128/924 J; 128/924 K; 623/23
[58] Field of Search ..................... 623/16, 20, 21, 22, 623/23, 1, 11; 128/92 Y, 92 YK, 92 YV, 92 VJ, 92 YF

[56] References Cited

U.S. PATENT DOCUMENTS

| 2,537,070 | 1/1951 | Longfellow | 128/92 YK |
| 4,501,269 | 2/1985 | Bagby | 128/92 YJ |

FOREIGN PATENT DOCUMENTS

| 0179736 | 4/1986 | European Pat. Off. | 623/22 |
| 0235606 | 9/1987 | European Pat. Off. | 623/22 |
| 2933271 | 3/1981 | Fed. Rep. of Germany | 623/22 |
| 1287526 | 2/1962 | France | 623/22 |
| 2189150 | 10/1987 | United Kingdom | 623/1 |

Primary Examiner—Richard J. Apley
Assistant Examiner—David J. Isabella
Attorney, Agent, or Firm—Edward S. Irons

[57] ABSTRACT

The invention replaces the natural joint structure with a porous globe structure, filled with bone graft, that is attached to a prosthetic shaft. The bone graft on the globe structure as it matures provides continuous bone structure which in combination with the globe structure provides a load sharing combination.

2 Claims, 2 Drawing Sheets

PROSTHETIC BONE JOINT

This application is a continuation of Ser. No. 042,511 filed Apr. 22, 1987 which is a continuation of Ser. No. 831,583 filed Feb. 21, 1986, both abandoned.

BACKGROUND OF THE INVENTION

1. Field of the Invention

This invention concerns reconstructive surgery of joints for the formation of movable joints and relates more particularly to implanting of a cup and head or ball replacement on a bone with the cup and head or ball replacement structure arranged for growth of bone graft material. Either a head or ball can be implanted or in combination with a cup. The invention is directed to treatment of hip and shoulder ailments including: arthritis; avascular necrosis; femoral and acetabular dylasias; revision of joint fusion; and, subcapital and cervical fractures of the femur.

2. Description of the Prior Art

Various techniques for joint replacement arthroplasties are known and currently in routine usage. Those of interest here are the hemi-arthroplasties type where the head or ball for the joint is replaced. Such surgery can be divided into three subcategories which relate to the methods for affixing implants to a bone.

One of these affixation methods relies on intramedullary implantation. An example of such a method is shown in U.S. No. Pat. 4,031,571 where the thigh portion of an endoprosthesis for a hip joint is provided with stepped projecting surfaces to distribute forces to bone tissue. A variation of this method includes the use of pins or screws to fix heads or balls to the shafts of bones.

Another method of fixation is the use of a side plate secured by screws to the main shaft of a bone and the mounting of an artificial head or ball to the side plate. Such plates are also used to mount repaired, original heads. Use of side plates and securing pins to mount heads on bones is a well known technique as is shown in U.S. Pat. Nos. 2,612,159; 2,699,774; 2,702,543; 2,834,342; and 4,236,512.

The final method of fixation in use today is cementing an artificial or a repaired, original head to a bone. Polymethyl methacrylate is a cement commonly used for cementing heads or balls to bones.

SUMMARY OF THE INVENTION

The basic problem inherent to all known methods of fixing heads or balls to bones is their susceptibility to structural failure. An unavoidable cause of the problem is the discrepancy in the modulus of elasticity betweeen bone and metal implants. This discrepancy is exacerbated by the arrangement of currently used implants in that the forces across the joint are transmitted first to the implant arrangement and then to the bone.

The present invention replaces the head or ball with a bone graft head or ball supported by a globe structure attached to a shaft. To mount the globe to the bone the original head is amputated and a hole is bored longitudinally through the neck located at the base where the head or ball had been attached. The hole is bored to the other side of the bone opposite the original location of the head or ball. Fastened to the shank of the bone is a side plate. This side plate is so located that the globe shaft when inserted in the bored hole also mates with a corresponding hole in the side plate. By use of a keyed portion on the globe shaft and a matching keyed portion in the mating hole in the side plate the globe shaft is prevented from rotating. The bone graft on the globe structure as it matures also grows into the neck of the original bone, and provides a continuous bone structure which in combination with the metal structures provides a load sharing combination and not an arrangement with the load directly transmitted via the metal implant to the bone.

This invention is useful for surgical formation of joints such as those of the hip or shoulder.

BRIEF DESCRIPTION OF THE DRAWINGS

These and other objects, advantages and novel features of the present invention will be more readily apprehended from the following detailed description when read in conjunction with the appended drawings, in which.

In the drawings corresponding components are designated by the same reference numerals throughout the various figures.

DETAILED DESCRIPTION OF THE INVENTION

As a preferred embodiment of the invention an implant for a hip joint is shown. However, use of the invention for other joints such as shoulder joints is directly applicable.

Figure 1:
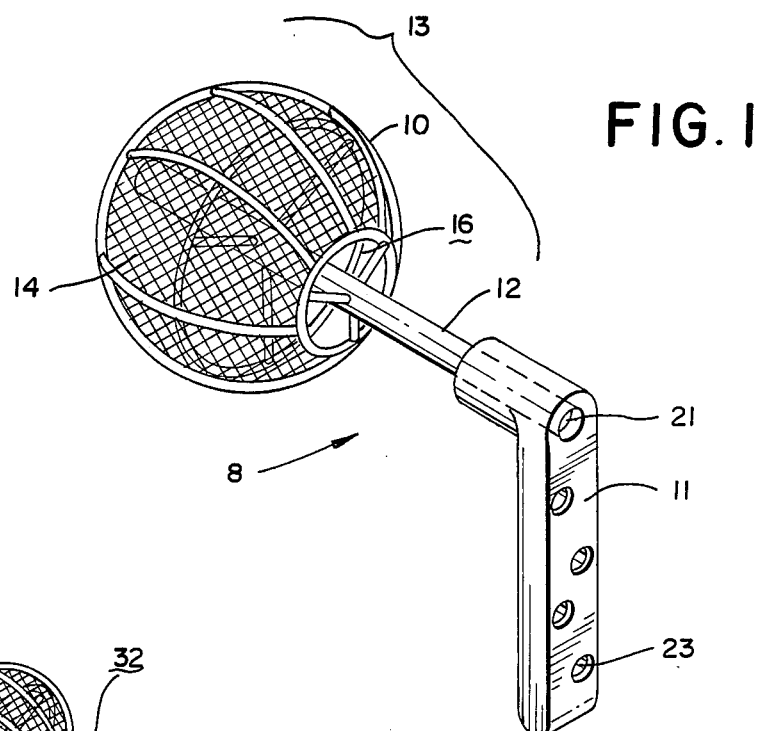
FIG. 1 is a perspective view of a joint implant according to the present invention.
Figure 2:
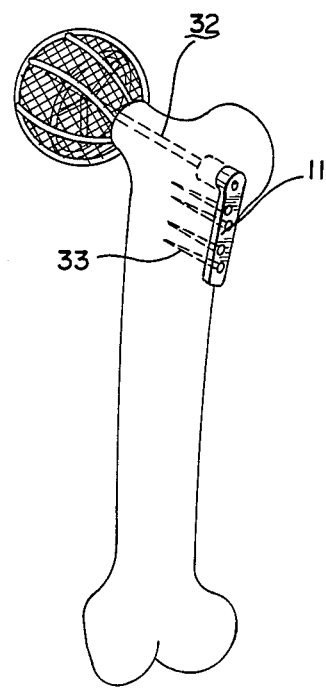
FIG. 2 is a perspective view of a joint implant according to the present invention mounted on a femoral bone.

An implant 8 for a hip joint according to the invention is shown in perspective in FIG. 1. The implant 8 includes a side plate 11, which acts as a force neutralizing plate, and a globe 13, which acts as a proximal femoral prosthesis. As shown in FIG. 1, the globe 13 is attached to the side plate 11 by a shaft 12. Another view of the implant for a hip is shown in FIG. 2 as the side plate 11 and globe 13 would be attached to the proximal femur.

To use the invention a surgeon would expose the hip, resect the femoral head adjacent the neck and dislocate the hip to expose the acetabulum. If an acetabulum cup, as explained below is to be inserted, the acetabulum would be reamed in order to denude the cartilage and to expose the subchondral bone.

The globe 13 can be fabricated from molded surgical stainless steel. Other metals such as titanium can also be used. The spherical surface of the globe 13 is formed by struts 10 and by a plastic mesh 14 mounted between the struts 10. The mesh 14 can be made of such synthetic flexible materials as polyethylene. At the base of the globe 13 adjacent shaft 12 re openings 16 for packing the globe 13 with bone graft material. The globe is in fact packed through openings 16 with bone graft material by morselizing the femoral head into cancellous chips. Should more bone graft material be needed, a bone graft could be harvested from the iliac crest or obtained from a bone bank.

Figure 3:
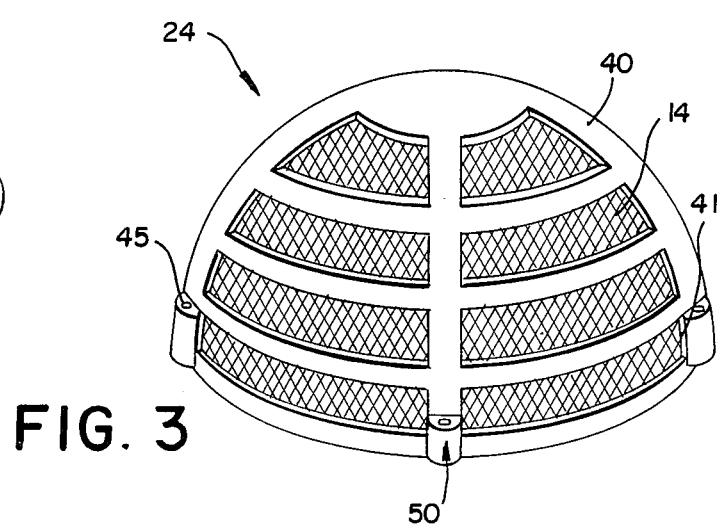
FIG. 3 is a side view of an acetabular cup component according to the present invention.
Figure 4:
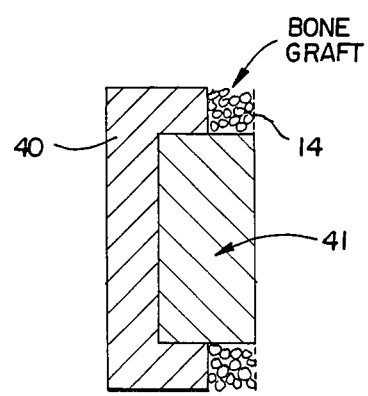
FIG. 4 is a sectional view of a strut with associated liner and mesh for an acetabular cup component according to the present invention; and, FIG. 5 is a perspective view of a side plate with a sectional view of a globe shaft according to the present invention.

Next an acetabular cup component 24 also formed from molded metal struts 40, see FIG. 3, and a polyethylene lining 41 adjacent each strut 40 and polyethylene mesh 14 in the spaces between the metal struts 40, see FIG. 4, is packed with bone graft material as is the globe 13. The bone graft material is packed about the acetabular cup component 24 so that the acetabular cup component 24 can be pressed into the acetabular socket and maintained in position with screws inserted through holes 45.

Figure 5:
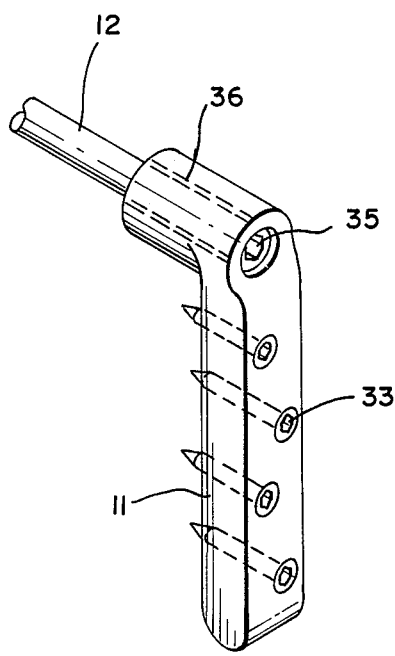

Now the side plate 11 is affixed to the lateral femoral shaft with appropriate length screws 3. The globe 13 is then by means of shaft 12 mounted on the neck of the femur through a hole 32 bored through the neck of the femur. To maintain the globe 13 on the femur a locking bolt 35, see FIG. 5, is attached to the end of the globe shaft 12. Rotation of globe 13 in the hole 32 bored in the femur neck is prevented by a keying system such as having shaft 12 be partially round with a flat surface dimensioned to mate with a corresponding flat surface in side plate 11 hole 36.

The hip is now reduced and the wound closed.

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A ball joint prosthesis comprising a ball joint, said ball joint comprising a hollow, globular structure defined by a plurality of spaced struts having porous mesh mounted therebetween, said struts and said mesh forming the globular surface of said structure and an orifice for the introduction of bone graft material into the hollow interior of said structure, and means for securing said structure to the bone joint from which the natural ball of a joint has been resected.

2. A prosthetic bone joint comprising a ball joint prosthesis and an acetabular cap prosthesis, said ball joint prosthesis comprising a hollow, globular structure defined by a plurality of spaced struts having porous mesh mounted therebetween, said struts and said mesh forming the globular surface of said structure and an orifice for the introduction of bone graft material into the hollow interior of said structure, and means for securing said structure to the bone joint from which the natural ball of a joint has been resected, and said acetabular cap prosthesis comprising a simulated acetabular cap structure, said structure being defined by a plurality of struts having porous mesh therebetween, said struts and said mesh forming the surface of said structure.

* * * * *